(12) United States Patent
Okandan et al.

(10) Patent No.: US 9,410,931 B1
(45) Date of Patent: Aug. 9, 2016

(54) MINIATURIZED PHOTOACOUSTIC SPECTROMETER

(71) Applicant: Sandia Corporation, Albuquerque, NM (US)

(72) Inventors: Murat Okandan, Edgewood, NM (US); Alex Robinson, Albuquerque, NM (US); Gregory N. Nielson, Albuquerque, NM (US); Paul J. Resnick, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 366 days.

(21) Appl. No.: 14/056,863

(22) Filed: Oct. 17, 2013

(51) Int. Cl.
 *G01N 29/36* (2006.01)
(52) U.S. Cl.
 CPC ........................... *G01N 29/36* (2013.01)
(58) Field of Classification Search
 CPC ..................... G01N 21/1702; G01N 29/02
 USPC ............................. 73/584, 655, 24.02
 See application file for complete search history.

(56) References Cited

U.S. PATENT DOCUMENTS

| | | | | |
|---|---|---|---|---|
| 4,412,105 A * | 10/1983 | Muscatell | ............... | H04R 5/027 381/172 |
| 5,194,847 A * | 3/1993 | Taylor | .................... | G01H 9/004 340/541 |
| 6,662,627 B2 | 12/2003 | Arnott et al. | | |
| 7,245,380 B2 * | 7/2007 | Kosterev | ............ | G01N 21/1702 250/343 |
| 7,886,576 B2 | 2/2011 | Uber | | |
| 8,240,189 B2 * | 8/2012 | Myrick | .............. | G01N 21/3504 73/24.02 |
| 8,451,447 B2 | 5/2013 | Fritz et al. | | |
| 2002/0093658 A1 * | 7/2002 | Han | ................... | G01N 21/1702 356/432 |
| 2004/0095570 A1 * | 5/2004 | Stanimirov | .......... | G01R 15/247 356/128 |
| 2010/0139368 A1 * | 6/2010 | Kotovsky | ........... | G01N 21/1702 73/24.06 |
| 2011/0154884 A1 * | 6/2011 | Weppenaar | ........... | F16L 11/082 73/24.02 |
| 2012/0055232 A1 | 3/2012 | Thorson | | |
| 2012/0272719 A1 | 11/2012 | Rezachek | | |
| 2013/0142519 A1 * | 6/2013 | Iwamoto | .............. | H04R 23/008 398/133 |

* cited by examiner

*Primary Examiner* — J M Saint Surin
(74) *Attorney, Agent, or Firm* — Medley, Behrens & Lewis, LLC; Aman Talwar (57) ABSTRACT

A low-power miniaturized photoacoustic sensor uses an optical microphone made by semiconductor fabrication techniques, and optionally allows for all-optical communication to and from the sensor. This allows integration of the photoacoustic sensor into systems with special requirements, such as those that would be reactive in an electrical discharge condition. The photoacoustic sensor can also be operated in various other modes with wide application flexibility.

20 Claims, 9 Drawing Sheets

MINIATURIZED PHOTOACOUSTIC SPECTROMETER

STATEMENT OF GOVERNMENTAL INTEREST

This invention was developed under Contract DE-AC04-97AL85000 between Sandia Corporation and the U.S. Department of Energy. The U.S. Government has certain rights in this invention.

BACKGROUND

Photoacoustic spectroscopy (PAS) relies on the photoacoustic effect in irradiating a sample with intermittent pulses of light. Concomitantly, as the incident light hits the sample, heat is generated, and acoustic waves having a frequency relative to the light pulse frequency are generated. The resulting series of acoustic pulses is detected by a highly sensitive microphone (for example at lkHz repetition rate) and may be formulated into a signal for analysis and detection of chemical species.

Optical microphones rely on modulated light from a displaced or vibrating microphone membrane and detecting the modulation of the light. The modulated light pattern carries the displacement information that is provided by the microphone membrane. By knowing the stiffness of the microphone membrane, the displacement can then be translated into a known pressure signal.

SUMMARY

The following is a brief summary of subject matter that is described in greater detail herein. This summary is not intended to be limiting as to the scope of the claims.

A low-power miniaturized photoacoustic sensor described herein employs an optical microphone made by semiconductor fabrication techniques, and optionally allows for all-optical communication to and from the sensor. This allows integration of the photoacoustic sensor into systems with special requirements, such as those that would be reactive in an electrical discharge condition. The photoacoustic sensor can also be operated in various other modes with wide application flexibility.

In an exemplary embodiment, the photoacoustic sensor includes a sample chamber, an optical fiber in optical communication with the sample chamber, and a microphone comprising a microphone membrane in acoustic communication with the sample chamber. The optical fiber is configured to direct the light to the sample chamber. A second optical fiber is also optionally included, and is configured to transmit a modulated light pattern from the light incident on the microphone membrane.

In an embodiment, the photoacoustic sensor uses the light that is directed into a sample chamber to impinge on the analyte and induce an acoustic wave. Additionally, the light is diffracted onto the microphone membrane to induce a characteristic modulated light pattern. This modulated light pattern may be transmitted optically to a remote computing device for analysis.

A method for photoacoustically analyzing an analyte is provided, and a method for making a miniaturized optical microphone component by semiconductor fabrication techniques is provided as well.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to a miniaturized photoacoustic sensor are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. Further, it is to be understood that functionality that is described as being carried out by a single system component may be performed by multiple components. Similarly, for instance, a single component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" may encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Additionally, as used herein, the term "exemplary" is intended to mean serving as an illustration or example of something, and is not intended to indicate a preference.

In an embodiment, a miniaturized photoacoustic sensor is optimized for applications where the volume available for sensor integration is limited and electrical connections to the sensing area are not desirable. The sensor, measured apart from any connecting cables, may, for example, have a total volume of 1 cubic millimeter to 1 cubic centimeter, such as, for example, 15 cubic millimeters to 800 cubic millimeters, or 60 cubic millimeters to 500 cubic millimeters. The sensor may be manufactured in such small dimensions by employing semiconductor fabrication techniques in the manufacture of components including the photoacoustic microphone.

Environments where the electrical connection-free embodiment may be particularly useful include those with unstable or reactive chemical species, such as volatile gas environments. The sensor may also be useful in analyzing chemicals in environments where an electrical spark or discharge could cause the analyte to react and change, thereby hampering accurate analysis of the analyte.

In an exemplary embodiment, the miniaturized photoacoustic sensor is also capable of operating at very low power. For example, the sensor may be configured to operate, for example at 1 mW to 100 mW, such as 5 mW to 75 mW, or 25 mW to 60 mW.

In another exemplary embodiment, the acoustic sensor of the miniaturized photoacoustic sensor is optically interrogated (light in-light out) and free of exposed electrical conductors on an exterior of the acoustic sensor (e.g., electrical wiring, conductors, or leads that are not hermetically sealed or encapsulated in the sensor) that might otherwise come into contact with the sample chamber or the environment in which the sensor is disposed. In embodiments, the light for generating the pressure pulse (through absorption by the chemical species of interest) is brought in by optical fiber. In a further enhancement, light provided by an optical fiber is converted into electrical power by a solar cell and is provided to an integrated circuit (IC) in the sensor. The IC controls the power delivery and runs local diagnostics, provides biasing (if necessary), and communicates data (for example, calibration and status information) back through the optical fiber by modulating a light source, such as an LED, VCSEL, or edge-emitting diode laser, maintaining the no-electrical conductor linkage between the sensor and the monitoring computing device.

Figure 1:
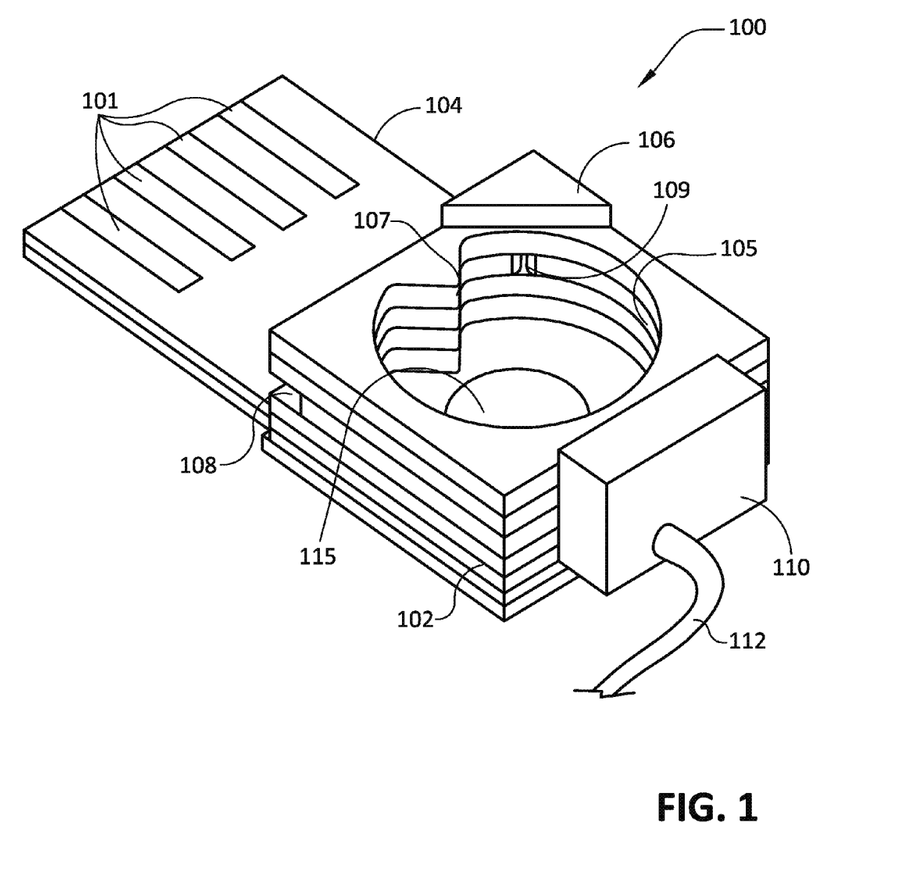
FIG. 1 is a cut-away perspective view of an exemplary photoacoustic sensor.

With reference now to FIG. 1, an exemplary system that facilitates photoacoustic analysis of a sample is illustrated. The system includes a photoacoustic sensor 100. In an embodiment, the photoacoustic sensor 100 is built on a base plate 104. The base plate 104 may comprise an acoustic insulator, such as ceramic, and the base plate 104 may house electrical connections, terminals, and components. In an exemplary embodiment, the electrical connections and components are hermetically sealed from the exterior of the photoacoustic sensor 100. In the embodiment of FIG. 1, the base plate 104 includes electrical contacts 101 that are configured to be electrically coupled to an external computing device, wherein the external computing device can perform functions such as testing, calibration, etc. on data received by way of the electrical contacts 101. However, the use of these contacts 101 (or any other electrical connection) is not required to operate the sensor 100 in a sample environment. In an embodiment, the electrical contacts 101 may be ports for respective optical fibers or may be replaced with ports for respective optical fibers. In another exemplary embodiment, the base plate 104 is not present, and components described as coupled to the base plate are directly coupled to each other.

An acoustic component 102 is secured on top of the base plate 104. The acoustic component 102 defines an inner sample chamber 105 that is covered with a top cover 106 (shown cut-away in FIG. 1). In an exemplary embodiment, the acoustic component 102 can comprise an acoustic insulator such as ceramic. The walls, top cover 106, and floor of the sample chamber 105 is coated with an optical reflector, such as gold, or another reflective metal. For instance, the reflector can be corrosion resistant and non-reactive with the sample environment in which the sensor is employed.

As shown in FIG. 1, the sample chamber 105 is an inner cavity bounded by components of the sensor 100. It is in the geometry of a hollow polygonal prism, which, as used herein, includes without limitation, a cylinder having a top and bottom. The sample chamber 105 of FIG. 1 is generally cylindrical with a triangular feature 107 extending out from the wall toward the center of the cylinder. The triangular feature promotes reflection of the light around the sample chamber 105, and additionally promotes absorption by the analyte.

The total volume of the sample chamber 105 may, for example, be 1 cubic millimeter to less than 1000 cubic millimeters, such as 10 cubic millimeters to 750 cubic millimeters, or 50 cubic millimeters to 250 cubic centimeters. The sample chamber may, for example, be 1 $mm^2$ to 10 $mm^2$ in base area, such as 2 $mm^2$ to 8 $mm^2$, or 3.5 $mm^2$ to 7.5 $mm^2$, and 1 mm to 10 mm in height, such as 2 mm to 8 mm or 3.5 mm to 7.5 mm.

The acoustic component 102 includes a sample inlet port 108 and a sample outlet port 109, wherein such ports 108 and 109 extend through the walls of the sample chamber 105 to the exterior of the photoacoustic sensor 100. The sample inlet and outlet ports 108 and 109 may be configured to couple to capillary tubing or other devices for transporting analytes. In an exemplary embodiment, the small size of the sample inlet and outlet ports 108 and 109 may enable such portions to function as respective capillaries. Further, the analyte may be pumped into the sample chamber 105, out of the sample chamber 105, or both. In yet another exemplary embodiment, the analyte may naturally diffuse in or out of the sample chamber 105 through the inlet and outlet ports 108 and 109 (e.g., no pump is needed).

A light component 110 is in optical communication with the sample chamber 105, and includes elements that facilitate direction of light into the sample chamber 105, including a prism, a mirror, a waveguide, or other suitable element. A pair of components are "in optical communication", as used herein, if they are aligned or positioned so that light can be directed between components of the pair. In FIG. 1, the light component 110 is coupled to the sample chamber 105 and forms a portion of the sample chamber 105 wall, thereby enclosing it. The light component 110 may comprise an IR fiber ferrule, and can be configured to receive an optical fiber 112. In an exemplary embodiment, the light component 110 connects to the optical fiber 112 and directs light pulses comprising infrared light from the optical fiber 112 into the sample chamber 105. In the exemplary embodiment shown in FIG. 1, the light component 110 is situated opposite to the triangular feature 107 of the wall of the sample chamber 105.

The light component 110 may also include a solar cell (not shown) that receives the light pulses from the optical fiber 112, or a separate optical fiber, or both. The solar cell converts optical signals into electrical current to power certain components of the photoacoustic sensor 100. These components may include, for example an IC coupled to the photoacoustic sensor 100, a transmitting light source coupled to the photoacoustic sensor 100, or a gating mechanism for the inlet and outlet ports 108 and 109.

The photoacoustic sensor 100 can also optionally include an IC that may be housed in the base plate 104 or coupled to another component of the photoacoustic sensor 100. The solar cell may be coupled to and provide current to such IC, wherein the IC is configured to provide power, instructions, or both power and instructions to components of the photoacoustic sensor 100.

In an exemplary embodiment, power to the photoacoustic sensor 100 is provided from a DC component of the optical signal as received by the solar cell and instructions are provided from an AC component from the optical signal, wherein the AC component is transmitted to the above-mentioned IC. For instance, the optical fiber 112 may transmit the light for the AC component that provides instructions to the IC, and a separate optical fiber may provide light to the solar cell, which converts such light to DC current to power the components of the sensor 100. In an embodiment, a capacitively coupled node component detects the AC part of the signal.

A microphone 115 is in acoustic communication with the sample chamber 105 and is coupled to the bottom side of the base plate 104. Thus, the microphone 115 provides at least a portion of the bottom surface and encloses the sample chamber 105. The light component 110 and the light directed into the sample chamber 105 are orthogonal to the microphone 115.

Figure 2:
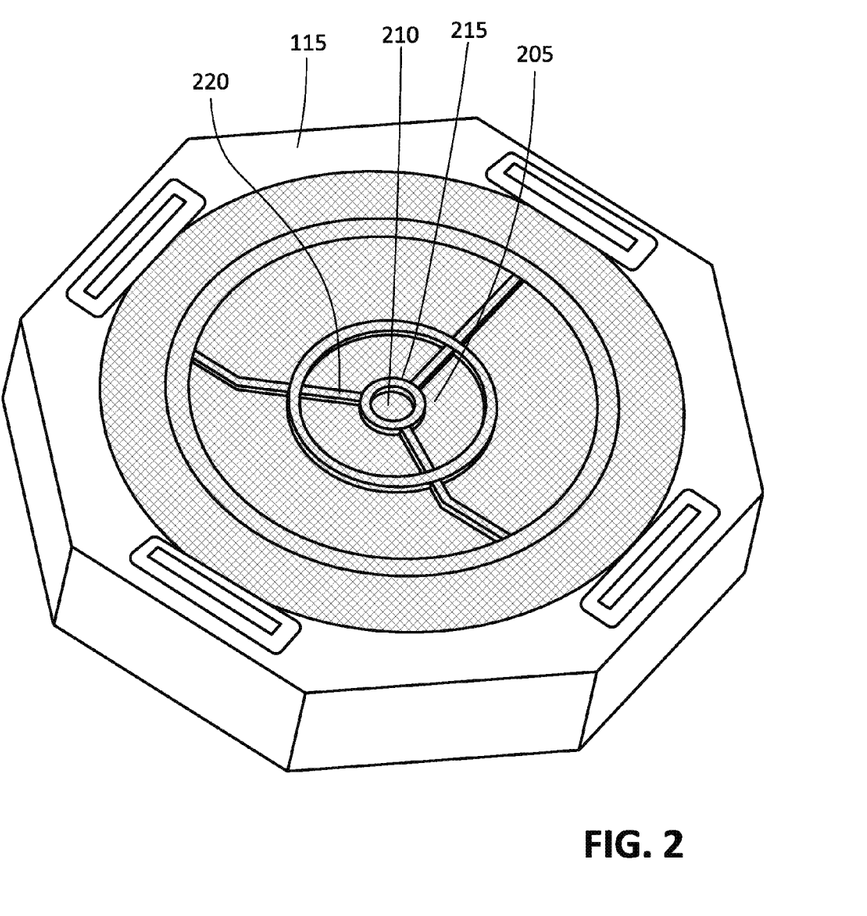
FIG. 2 is a perspective view of an exemplary microphone.

FIG. 2 shows further detail of the microphone 115. Pursuant to an example, the microphone 115 is an optical microphone and comprises a microphone membrane 205 and a diffraction grating 210. The microphone membrane 205 and/or the diffraction grating 210 can be coated with a reflective coating, such as gold. (FIG. 7B also shows a cross-sectional view of the microphone membrane 205 and diffraction grating 210.) The diffraction grating 210 is held over the microphone membrane 205 by a support ring 215 suspended by a support arm 220. The diffraction grating 210 is positioned below the microphone membrane 205. The diffraction grating 210 causes light coming from a displacement interrogation optical fiber to diffract onto the microphone membrane 205. The positioning of the displacement interrogation optical fiber 1160 in an embodiment is depicted in FIG. 7B. As the microphone membrane 205 is displaced and vibrated from the acoustic pulses from the sample chamber 105, a modulated light pattern is generated.

In another embodiment, the diffraction grating 210 is positioned above the microphone membrane 205. The diffraction grating 210 causes a portion of the light coming from the sample chamber 105 to diffract onto the microphone membrane 205.

In an embodiment, the microphone 115 includes an optical component 1150 (shown in FIG. 7B) for detecting the modulated light pattern or transmitting optical output. Thus, the optical component 1150 can be or include an optical fiber that directly transmits the diffracted light pattern to the external computing device (thereby providing an optical output signal from the photoacoustic sensor 100), a photodetector that detects the diffracted light pattern (such as a photodiode), and/or other elements that facilitate detection and/or transmittal of the diffracted light pattern. Such optical fiber can have prisms, mirrors, or other optical elements associated therewith to facilitate transmittal of the optical output signal to a remotely situated computing device. Additionally, one or more lenses, mirrors, lensed fibers, or waveguides that focus the diffracted light on the optical fiber or photodetector may also be employed. In an exemplary embodiment, a plurality of optical fibers can be configured to receive respective diffracted light patterns simultaneously, and can be employed to transmit the diffracted light patterns to the remotely situated computing device or respective photodetectors. Still further, an optical signal that encodes data can be transmitted to or from the photoacoustic sensor 100 by way of at least one optical fiber, such as the optical component 1150. Exemplary positioning of the optical component 1150 relative to the diffraction grating 210 and the microphone membrane 205 is depicted in FIG. 7B.

In an embodiment where the photodetector is used to detect the diffracted light, the photodetector may transmit an electrical signal to an output light source coupled to the sensor 100. The output light source, may be, for example, an LED, a laser, or a vertical cavity surface emitting laser (VCSEL). The optical output signal is then transmitted through an optical output fiber coupled to the output light source.

In an alternative embodiment, the microphone 115 is a piezoelectric microphone where the acoustic response is measured piezoelectrically. In such an embodiment, a signal converter is used to convert the piezoelectric impulses to an output light source coupled to the sensor 100, and an optical signal is transmitted through an optical output fiber coupled to the light source.

The system may further include an external computing device (which is explained in further detail below) that is used to analyze the optical output signal or electrical output from the photoacoustic sensor 100.

The integrated circuit that is onboard the sensor 100 may receive electrical input from the photodetector or a piezoelectric microphone, and perform onboard measurements, calibrations, or other processing of the input. The integrated circuit then communicates data through an electrical signal to the output light source coupled to the sensor 100, and an optical output signal is transmitted through the optical output fiber coupled to the light source. The optical output signal may thus be defined as comprising data relating to the modulated light pattern, which may directly reflect the modulated light pattern or may be processed data relating to the modulated light pattern.

In another exemplary embodiment, the light component can include a laser. Light emitted by the laser that is incident on a grating can be modulated by the relative movement of the grating and a reflector surface that is proximate to the grating. A related alternative approach is based on modulation of laser light in a waveguide that is mechanically deformed due to the incident pressure pulse. In order to reduce possible system noise, the sensor can be modulated at a higher frequency and filtered to remove the unwanted noise sources. This can be achieved by modulating light emitted by the laser that is directed to the chemical species and/or by modulating light emitted by a laser that is interrogating the acoustic sensor. In yet another alternative embodiment, the sensor can be mechanically modulated (for example, by electrostatically moving the grating).

FIGS. 3-8 illustrate exemplary methodologies relating to analyzing an analyte photoacoustically (FIG. 3) and making a miniaturized optical microphone by semiconductor manufacturing techniques (FIG. 4-8). While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Figure 3:
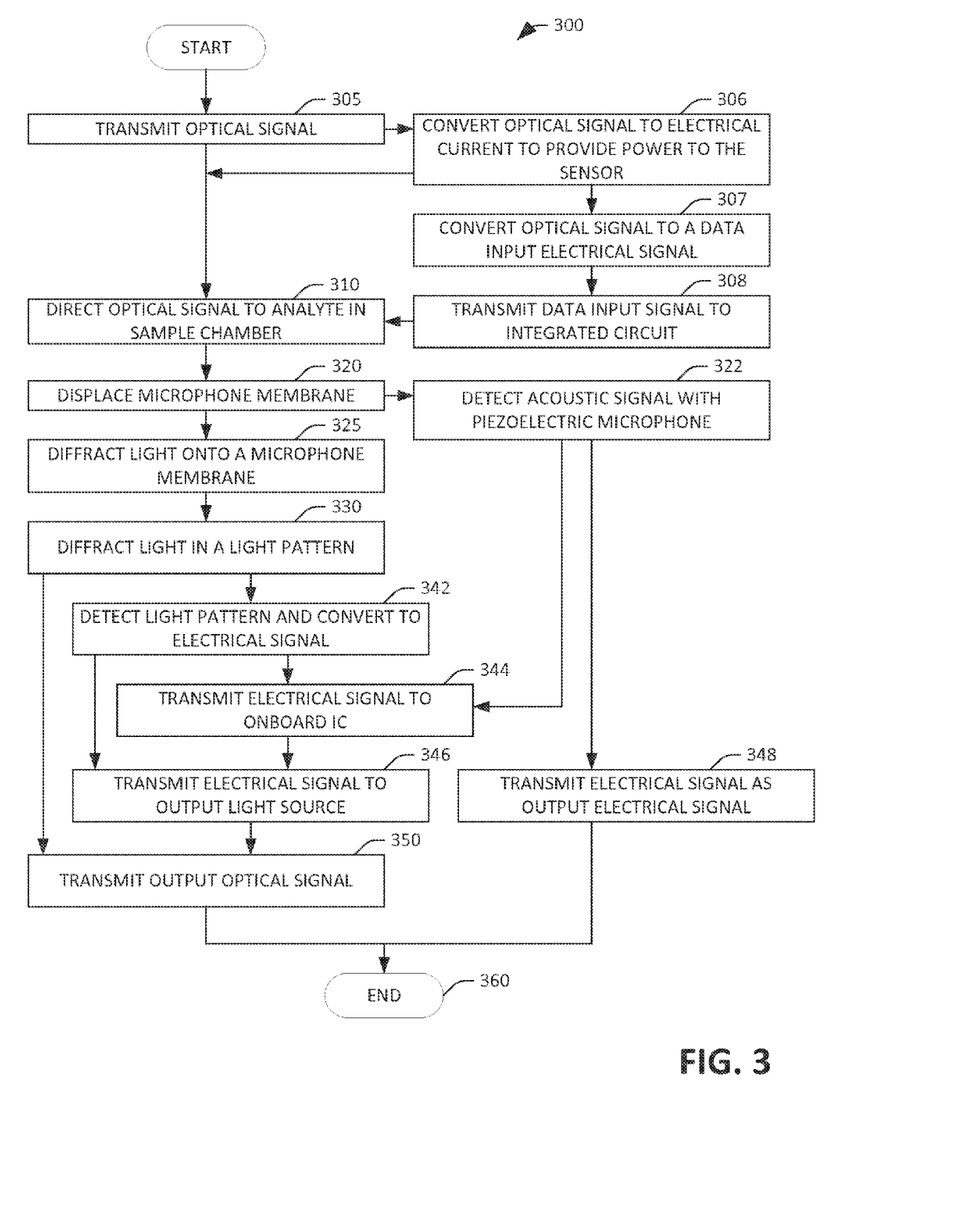
FIG. 3 is a flow diagram of an exemplary methodology for photoacoustical analysis.

Referring now solely to FIG. 3, a methodology 300 that facilitates photoacoustic analysis is illustrated. The methodology 300 begins at 301, and at 305, an optical signal is transmitted to a photoacoustic sensor, through, for example, an optical fiber. At 310, the optical signal is directed into a sample chamber of the sensor, where an acoustic signal is induced when the light interacts with an analyte. At 320, the acoustic signal displaces the microphone membrane, causing a vibration response.

At 325, light from the optical signal is diffracted onto the microphone membrane. For example, a portion of the light is diffracted as it passes from the sample chamber through a diffraction grating and onto the microphone membrane. In another exemplary embodiment, a separate light source is used to interrogate the microphone membrane.

At 330, the displacement of the microphone membrane causes light incident on the microphone membrane to be diffracted in a modulated light pattern that is relative to the displacement. At this point, the modulated light pattern may optically be received through, for example, a lens or waveguide coupled to an optical fiber, and at 350 the modulated light pattern can be transmitted as an optical output signal 350 outside the sensor.

Optionally, at 342, the modulated light pattern may instead or in addition be detected with a photodetector, which converts the modulated light pattern to an electrical signal. At 344, the electrical signal may be transmitted to the IC for processing, or at 346 the electrical signal can be transmitted to an output light source for optical transmission, where the modulated light pattern or data indicative thereof is transmitted as an output optical signal at 350. In another exemplary embodiment, the modulated light pattern is directly output through optical fibers, and the signal that is processed by the IC is for providing one or more of a state of health, calibration, or diagnostics type of information.

In another alternative along this path, the electrical signal from the photodetector or from the integrated circuit may be transmitted as electrical output 348. However, this is not preferred for applications in volatile environments. This option may be used, for example to calibrate and test the sensor prior to inserting it into a testing environment.

In another embodiment, after act 320, at 322 displacement of the microphone membrane can detected on a piezoelectric microphone, which converts the acoustic signal to an electrical signal. This electrical signal may then be transmitted at 348 as an output electrical signal (or the methodology 300 can proceed to acts 344, 346, 348, and 350).

In another embodiment depicted as an option in the methodology 300, the photoacoustic sensor is powered and controlled by an optical linkage. At 306, a transmitted optical signal is received by a solar cell on the photoacoustic sensor and converted to electrical current to provide power to the sensor. At 307, the same or a different optical signal may be converted to a data input signal, and this signal is then transmitted to the integrated circuit at 308. The methodology 300 can then proceed to act 310. In an exemplary embodiment, both AC and DC current can be generated from the same optical input signal carried over an optical fiber. In such embodiment, the optical signal has been modulated to encode data therein. The DC portion of the optical signal is converted to electrical power by the solar cell and the AC part of the signal can be detected by a capacitively coupled node that only detects the AC part of the signal. Whereas the sensor can also or alternatively be powered through an electrical connection, such an electrical connection is not preferred when the sensor is deployed in certain testing environments.

In a method of analyzing a sample with the miniaturized photoacoustic sensor, no electrical signals are passed between the sensor and an exterior measurement point, such as a computing device. As mentioned above, this embodiment, where there are only optical linkages, is valuable when there is a concern about having an electrical conductor running between where the monitoring, processing, or observation is being made (the computing device) and the location of the sensor.

Referring now to FIGS. 4-8, a semiconductor manufacturing methodology for making an exemplary miniaturized optical microphone of the photoacoustic sensor is illustrated. This methodology is only an example, and other processes and steps may be used to manufacture embodiments of the miniaturized photoacoustic sensor. Terms such as etching, releasing, and deposition are used as those terms are typically used in semiconductor fabrication techniques. For example, deposition may be performed by processes such as physical vapor deposition (PVD), chemical vapor deposition (CVD), electrochemical deposition (ECD), molecular beam epitaxy (MBE), atomic layer deposition (ALD), etc. As another example, wet or dry etching may be used.

Figure 4A:
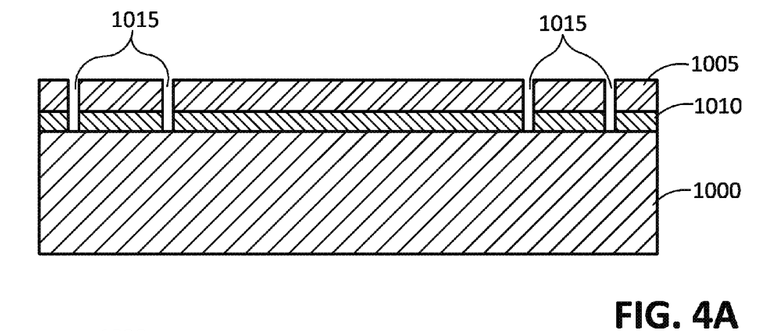
FIGS. 4-8 are successive cross-sectional views showing the steps of an exemplary semiconductor manufacturing method for making an exemplary microphone component.

In FIG. 4A, a silicon-on-insulator (SOI) wafer 1000 is provided. The upper-most layer disposed on the wafer 1000 is a device layer 1005, and the middle layer directly on top of the wafer 1000 is a buried silicon dioxide layer 1010. The device layer 1005 and the buried silicon dioxide layer 1010 are etched to form divots 1015. The device layer 1005 may be, for example, 20 microns to 1 micron, such as, for example, 5 microns to 15 microns. The oxide layer 1010 may be, for example, 0.5 microns to 2 microns, such as, for example, 1 micron to 1.5 microns.

Figure 4B:
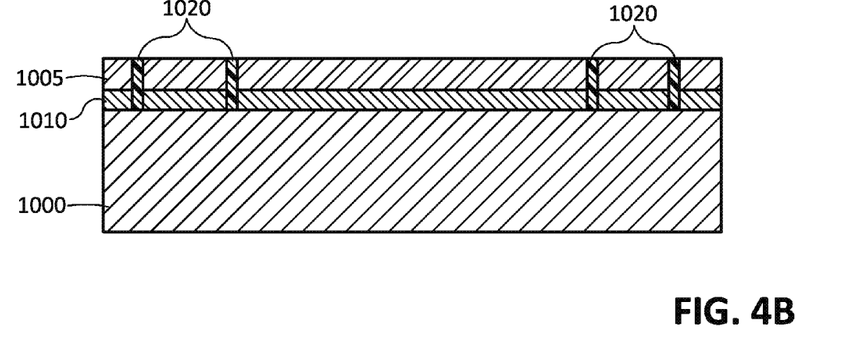

In FIG. 4B, the divots 1015 are backfilled to form doped-polysilicon-filled divots 1020 and then chemical/mechanical polishing is performed to remove excess polysilicon and to smooth out the topography. This chemical/mechanical polishing step may also be performed after other deposition or filling steps.

Figure 4C:
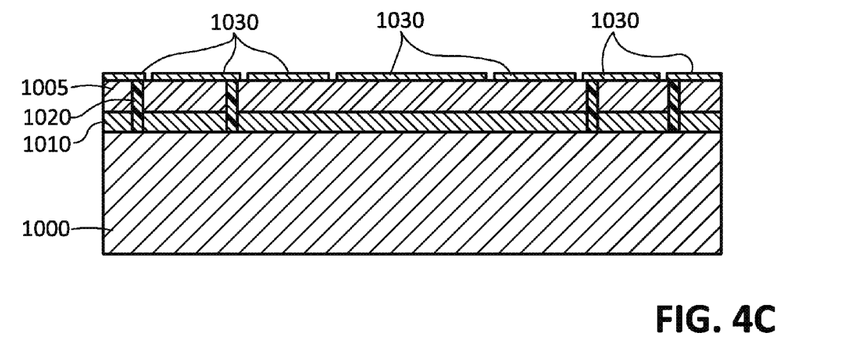

In FIG. 4C, a second oxide layer 1025 is deposited over the device layer 1005. The second oxide layer 1025 is then etched down to the device layer 1005 in six locations 1030, four that are in the middle between the doped-polysilicon-filled divots 1020 and one on each side that are between the outer and inner doped-polysilicon-filled divots 1020. The second oxide layer 1025 may be, for example 0.25 microns to 1 micron, for example, 0.4 microns to 0.75 microns. The same silicon dioxide exemplified above for the buried layer 1010, may be used for the second oxide layer 1025 and other oxide layers described below.

Figure 5A:
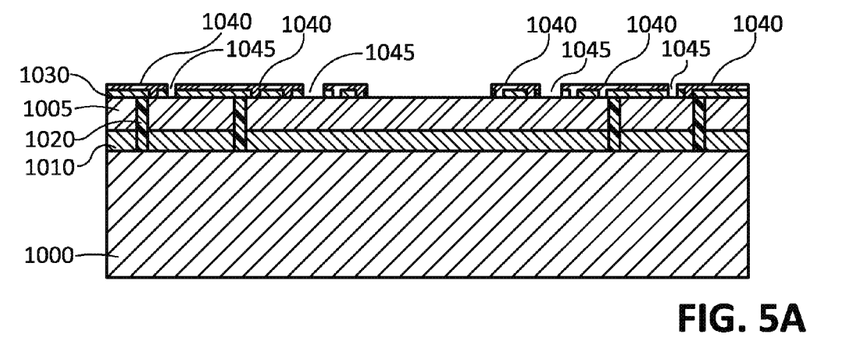

In FIG. 5A, a silicon nitride layer 1040 is deposited over the second oxide layer 1025 and the nitride fills in the etchings locations 1030 in the second oxide layer 1025. In addition, four etchings 1045 are performed to remove portions of both the second oxide layer 1025 and nitride layers 1040.

Figure 5B:
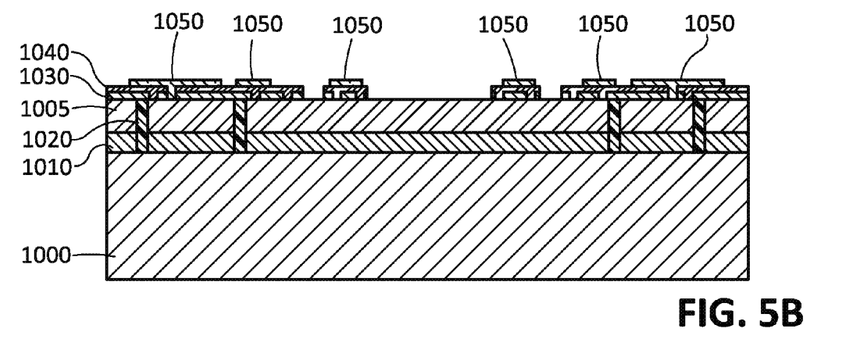

In FIG. 5B, a conductive (doped) polysilicon layer 1050 is then deposited over the nitride layer 1040, and also fills the outer two etchings 1045 in the second oxide layer 1025 and the nitride layer 1040. The polysilicon layer 1050 makes contact to the substrate to provide electrical connectivity to those regions. Further etchings are made in the polysilicon layer 1050 as shown in FIG. 5B.

Figure 5C:
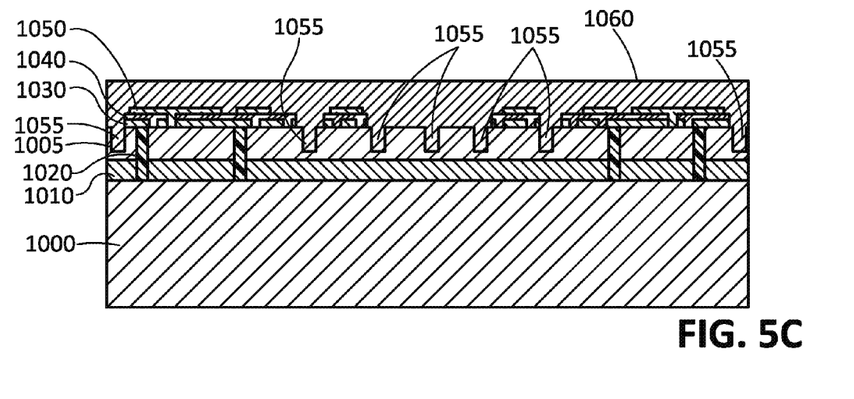

In FIG. 5C several additional etchings 1055 are made through the nitride, second oxide and device layers 1040, 1025, 1005 to open divots through the device layer 1005 and to contact the buried oxide layer 1010. This step allows for later removing device layer 1005 regions. A third oxide layer 1060 is deposited over the structure to encapsulate such structure. This third oxide layer 1060 may have a thickness, for example, of 1 to 5 microns, such as 1 to 3 microns, as measured over the polysilicon layer 1050.

Figure 6A:
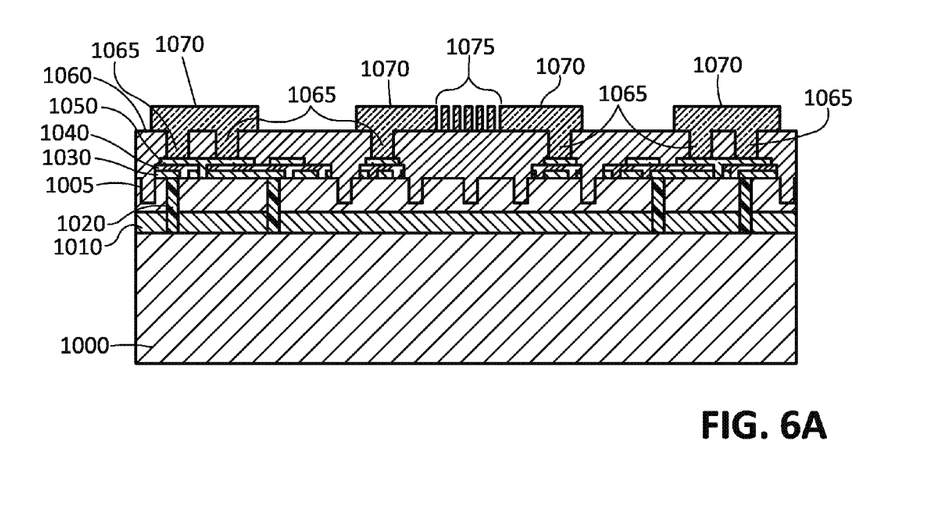

FIG. 6A shows contact holes 1065 etched in the third oxide layer 1060 with a second polysilicon layer 1070. The second polysilicon layer 1070 is patterned to form a diffraction grating 1075. In an embodiment, other features, such as posts, electrical connects, or other connections or features may be patterned as needed in the structure.

Figure 6B:
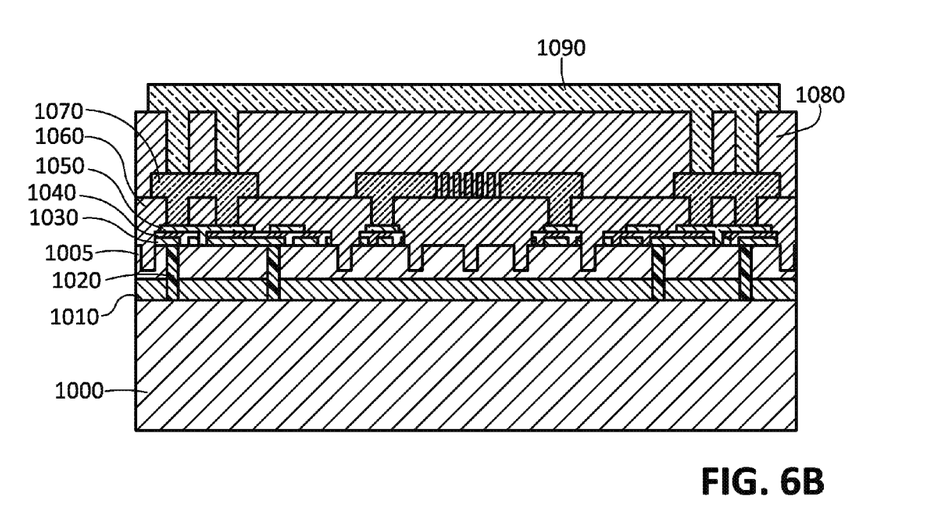

FIG. 6B shows a fourth oxide layer 1080, deposited over and contacting the second polysilicon layer 1070 and the third oxide layer 1060. The fourth oxide layer 1080 has a thickness of, for example, 2 to 10 micrometers, or 4 to 6 micrometers over the second polysilicon layer 1070. In an embodiment, etching is performed in four locations through the fourth oxide layer 1080 to the outer portions of the second polysilicon layer 1070. Chemical/mechanical polishing is performed, and then a third conductive polysilicon layer 1090 is deposited. In this case, the top polysilicon layer 1090 forms the membrane for the microphone.

Figure 7A:
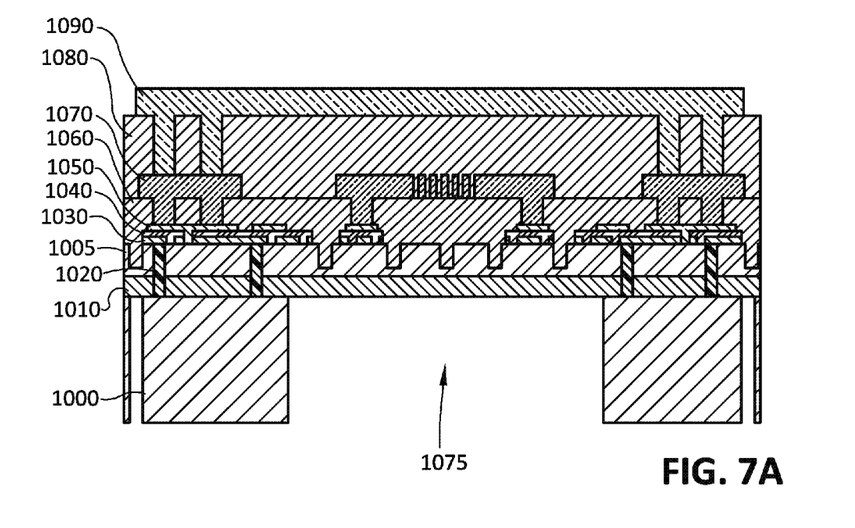
Figure 7B:
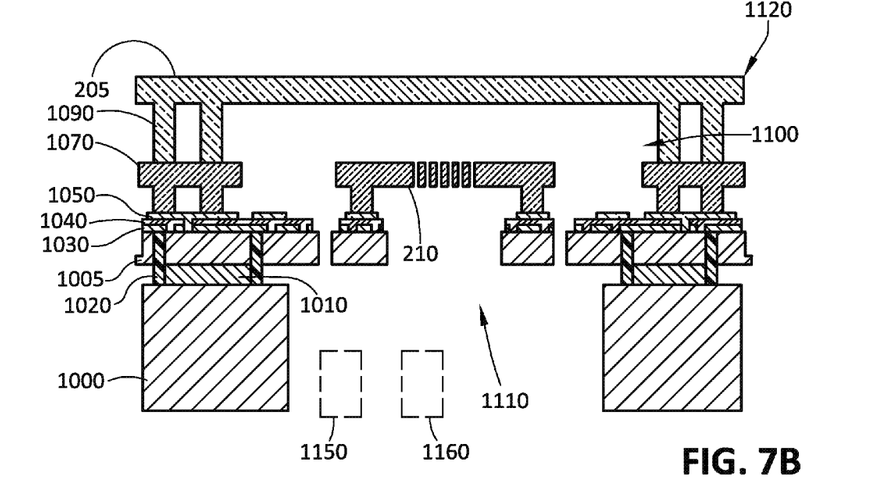

FIG. 7A shows the SOI wafer 1000 etched from the back forming a cavity 1095 exposing portions of the buried oxide layer 1010. In an embodiment, a Bosch etch process may be used for this step. Following a release etch, several additional layers are removed as is shown in FIG. 7B, and the device is singulated from the rest of the structure. This results in formation of a microphone cavity 1100 and an opening 1110 to the diffraction grating 1075 to what will be the control side of the sensor. Thus, an example miniaturized optical microphone 1120 is formed that may be picked up and assembled into a sensor system. FIG. 7B also depicts where an optical component 1150 and a displacement interrogation optical fiber 1160 may be positioned.

Figure 8A:
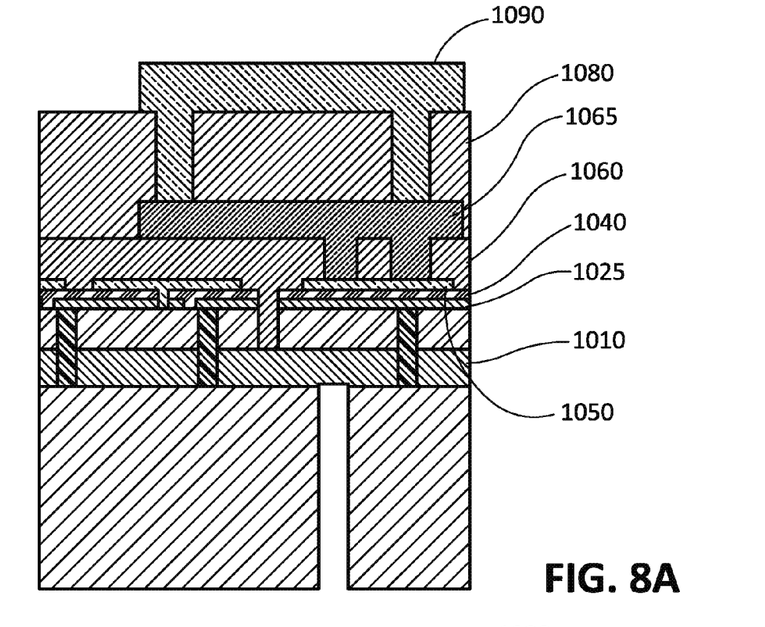
Figure 8B:
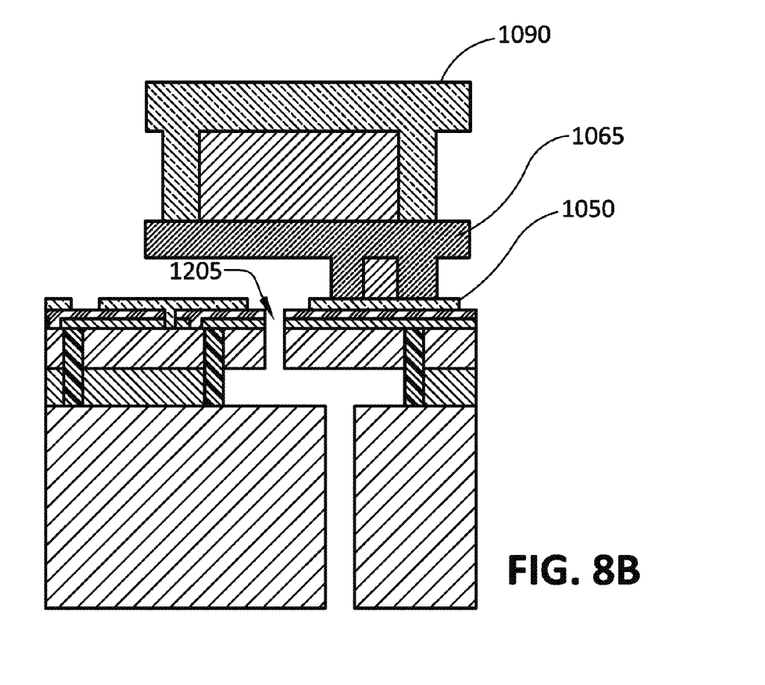

FIGS. 8A and 8B depict, in further detail, a singulation release method that uses Bosch etching to release the device from the wafer. A trench 1205 is etched and backfilled with oxide from the top side on the device. Then the Bosch etch, from the back, removes oxide from the trench 1205 to provide a mechanical capture of the device, so such device does not suffer an unsupported fall when the device is released. Then when the oxide is removed, the structure can then be moved up from the substrate.

The photoacoustic sensor may be optimized for gas-phase analytes or solution-phase analytes or even solid analytes. The photoacoustic sensor system may also be used, for example, to perform $CO_2$ detection in the atmosphere with high resolution and no consumables.

Figure 9:
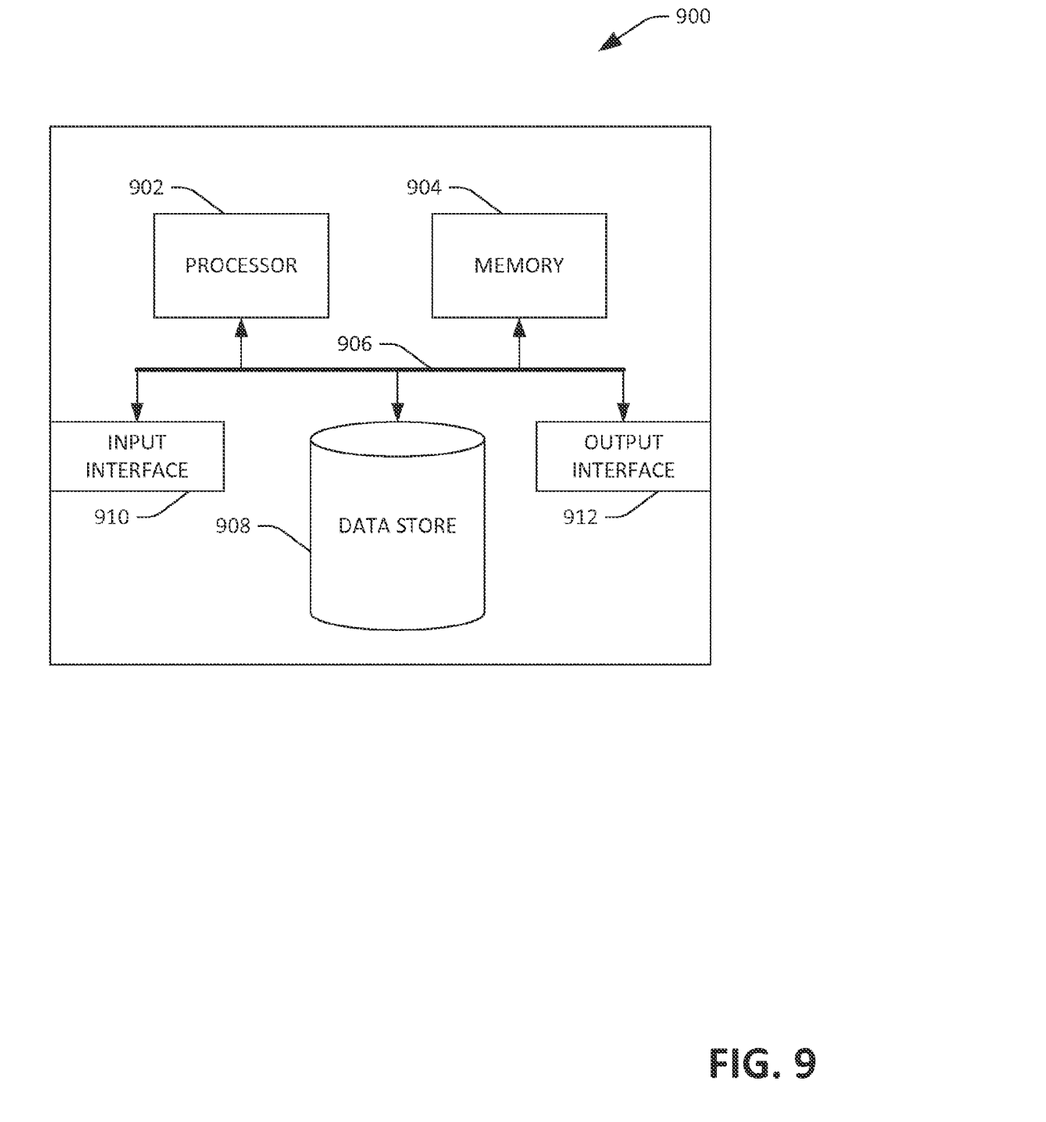
FIG. 9 is an exemplary computing device.

Referring now to FIG. 9, a high-level illustration of an exemplary computing device 2000 that can be used in accordance with the systems and methodologies disclosed herein is illustrated. For instance, the computing device 2000 may be used in a system to analyze the output signals from a miniaturized photoacoustic sensor. By way of another example, the computing device 2000 can be used in a system to calibrate and test the miniaturized photoacoustic sensor. The computing device 2000 includes at least one processor 2002 that executes instructions that are stored in a memory 2004. The instructions may be, for instance, instructions for implementing functionality described as being carried out by one or more components discussed above or instructions for implementing one or more of the methods described above or portions of the methods described above. The processor 2002 may access the memory 2004 by way of a system bus 2006.

The computing device 2000 additionally includes a data store 2008 that is accessible by the processor 2002 by way of the system bus 2006. The data store 2008 may include executable instructions, such as, for example, routines for calibrating and operating the sensor for transmittal to the integrated circuit on the sensor, instructions for analyzing the output signals from the sensor. The data store 2008 may also store raw or processed sensor output data. The computing device 2000 also includes an input interface 2010 that allows external devices to communicate with the computing device 2000. For instance, the input interface 2010 may be used to receive instructions from an external computer device, for example, from a user. The input interface 2010 may also receive input from one or more miniaturized photoacoustic sensors. The computing device 2000 also includes an output interface 2012 that interfaces the computing device 2000 with one or more external devices. For example, the computing device 2000 may display text or images, by way of the output interface 2012.

Additionally, although illustrated as a single system, it is to be understood that the computing device 2000 may be a distributed system. Thus, for instance, several devices may be in communication by way of a network connection and may collectively perform tasks described as being performed by the computing device 2000.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system comprising:
a photoacoustic sensor including:
a sample chamber, wherein the sample chamber is a cavity in a hollow polygonal prism with a microphone component coupled to and enclosing a bottom end of the cavity and a light source coupled to an opening in a wall of the cavity;

an optical fiber in optical communication with the sample chamber;

a microphone comprising a microphone membrane in acoustic communication with the sample chamber;

the optical fiber configured to direct light to the sample chamber; and an optical component configured to detect or transmit a light pattern from light incident on the microphone membrane.

2. The system of claim 1, wherein the microphone membrane is configured so the light incident on the microphone membrane is the light from the sample chamber.

3. The system of claim 2, further comprising a diffraction grating positioned to diffract the light onto the microphone membrane.

4. The system of claim 1, further comprising a solar cell configured to receive light from the optical fiber or another optical fiber.

5. The system of claim 4, further comprising an integrated circuit configured to provide power, instructions, or power and instructions to the sensor, wherein the solar cell is electrically coupled to the integrated circuit.

6. The system of claim 5, wherein the sensor is configured to receive power provided from a DC component of the light as received by the solar cell and configured to receive instructions from an AC component of the light.

7. The system of claim 5, further comprising:

an output light source and an optical fiber coupled to the output light source, the integrated circuit being in communication with the output light source.

8. The system of claim 1, wherein the optical component comprises an optical fiber that is configured to transmit the light pattern as an output optical signal.

9. The system of claim 1, wherein the sensor is free of exposed electrical wiring and conductors on an exterior of the sensor.

10. The system of claim 1, wherein the total volume of the photoacoustic sensor is 1 cubic millimeter to 1 cubic centimeter.

11. The system of claim 1, wherein the sensor operates at 1 mW to 100 mW.

12. The system of claim 1, wherein the sample chamber is configured for analyzing a gas.

13. The system of claim 1, wherein the microphone component is made by a semiconductor manufacturing process.

14. A system comprising:

a photoacoustic sensor including:

a sample chamber, wherein the sample chamber is 1 mm$^2$ to 10 mm$^2$ in base area, and 1 mm to 10 mm in height;

a first optical fiber configured to direct light to the sample chamber; and an optical microphone in acoustic and optical communication with the sample chamber, the optical microphone configured to be interrogated with at least a portion of the light from the sample chamber or from a second optical fiber; and a computing device in optical communication with the sensor through a third optical fiber.

15. The system of claim 14, wherein the sample chamber is a cavity in a hollow polygonal prism with a microphone component coupled to and enclosing a bottom end of the cavity and q light source coupled to an opening in a wall of the cavity.

16. The system of claim 14, wherein the total volume of the photoacoustic sensor is 1 cubic millimeter to 1 cubic centimeter.

17. The system of claim 14, wherein the sensor operates at 1 mW to 100 mW.

18. A method for photoacoustically analyzing an analyte in an environment, comprising:

transmitting an optical signal;

directing light from the optical signal to the analyte in a sample chamber;

inducing an acoustic signal from the analyte, the acoustic signal causing a displacement of a microphone membrane;

directing light onto the displaced microphone membrane, thereby inducing a light pattern;

transmitting an optical output signal comprising data relating to the light pattern;

detecting the light pattern with a photodetector and converting the light pattern to an electrical signal or detecting the acoustic signal with a piezoelectric microphone; and transmitting the electrical signal to an onboard integrated circuit for processing, wherein the data relating to the light pattern comprises processed data relating to the light pattern.

19. The method of claim 18, wherein the analyte or environment are reactive to an electrical discharge.

20. The method of claim 18, further comprising at least one of the following acts:

converting at least a portion of the optical signal or a separate optical signal to electrical current to provide power to the sensor; and/or converting at least a portion of the optical signal or a separate optical signal to a data input electrical signal and transmitting the data input electrical signal to an integrated circuit.

* * * * *